United States Patent [19]

Tanaka et al.

[11] Patent Number: 5,378,610
[45] Date of Patent: Jan. 3, 1995

[54] METHOD FOR ASSAYING ENDOTOXIN IN SERUM OR PLASMA USING LIMULUS AMOEBOCYTE LYSATE

[75] Inventors: Shigenori Tanaka; Hiroshi Tamura, both of Tokyo, Japan

[73] Assignee: Seikagaku Kogyo Kabushiki Kaisha (Seikagaku Corporation), Tokyo, Japan

[21] Appl. No.: 859,398

[22] PCT Filed: Sep. 27, 1991

[86] PCT No.: PCT/JP91/01309

§ 371 Date: May 28, 1992

§ 102(e) Date: May 28, 1992

[87] PCT Pub. No.: WO92/06382

PCT Pub. Date: Apr. 16, 1992

[30] Foreign Application Priority Data

Sep. 28, 1990 [JP] Japan ................. 2-257415

[51] Int. Cl.$^6$ .......................... C12Q 1/34; C12Q 1/00; C12Q 1/02
[52] U.S. Cl. ........................ 435/18; 435/7.21; 435/7.34; 435/7.4; 435/29
[58] Field of Search .............. 435/7.21, 7.34, 7.4, 435/18, 29

[56] References Cited

U.S. PATENT DOCUMENTS

| | | | |
|---|---|---|---|
| 4,096,091 | 6/1978 | Hopkins, II | 435/18 |
| 4,276,050 | 6/1981 | Firca | 435/18 |
| 4,322,217 | 3/1982 | Dikeman | 435/7.21 |
| 4,406,832 | 9/1983 | Mills | 435/18 |
| 4,495,294 | 1/1985 | Nakahara | 435/18 |
| 4,808,314 | 2/1989 | Karplus | 210/634 |

FOREIGN PATENT DOCUMENTS 080649  6/1983  European Pat. Off. ..... G01N 33/50

OTHER PUBLICATIONS

Chemical Abstracts, vol. 92, No. 21, May 21, 1980, abstract No. 17696 Du Bose, D. A. et al.
Chemical Abstracts, vol. 111, No. 11, Sep. 11, 1989, abstract No. 91769 Yajima, Y. et al.

*Primary Examiner*—Michael G. Wityshyn
*Assistant Examiner*—Ralph Gitomer
*Attorney, Agent, or Firm*—Sughrue, Mion, Zinn, Macpeak & Seas

[57] ABSTRACT

The present invention has been made in order to solve the problems in conventional methods of assaying an endotoxin in a specimen such as plasma or serum by the limulus test, which requires a complicated pretreatment procedure such as centrifugation for removing denatured precipitates formed with an acid treatment. According to the assay method of the present invention, an endotoxin adsorbed by proteins, lipids and platelets can be efficiently liberated simply by adding a mixed aqueous solution having a specific composition according to the present invention without any separation procedure and thus a sample solution of good qualities can be prepared. After adding the mixed aqueous solution containing a specific surfactant, a compound having an imidazolyl group or an amino group and an alkaline earth metal salt and an alkaline metal hydroxide to the specimen, followed by addition of the limulus amoebocyte lysate components, the endotoxin can be easily, quickly and precisely assayed. In particular, gram-negative bacterial septicemia, which can be hardly diagnosed, can be quickly assayed thereby.

6 Claims, No Drawings

METHOD FOR ASSAYING ENDOTOXIN IN SERUM OR PLASMA USING LIMULUS AMOEBOCYTE LYSATE

FIELD OF THE INVENTION

This invention relates to a method for assaying an endotoxin in plasma or serum. More particularly, it relates to pretreatment for assaying an endotoxin with high accuracy.

BACKGROUND OF THE INVENTION

There has been known a method for assaying an endotoxin by using limulus amoebocyte lysate components (hereinafter referred to as the limulus test), which has been frequently employed in the examination on the contamination of drugs and water and in clinical tests. The limulus test is suited for the detection of a trace amount of endotoxin in a biological specimen because of its high detection sensitivity.

A biological specimen contains an endotoxin adsorbed by, for example, proteins. It is therefore required prior to the limulus test to perform a pretreatment of the specimen so that the endotoxin could be efficiently liberated from the proteins. It is known to pretreat a biological specimen (for example, plasma, serum) containing granulocytes by treating a sample with an acid, having a pKa of 3 or below at 25° C., at a pH value of 3 or below, removing the denatured precipitate by centrifugation, collecting the supernatant and neutralizing it with an alkali to serve as a sample solution (JP-B-63-55671; the term "JP-B" as used herein means an "examined Japanese patent publication"). However this method is disadvantageous in that the separation procedure is complicated and requires a long period of time for completing the whole procedure and that the specimen would be possibly contaminated.

DISCLOSURE OF THE INVENTION

It is an object of the present invention to provide a method of efficiently, conveniently and rapidly assaying an endotoxin in plasma or serum with extremely high accuracy.

The present invention relates to a method of assaying an endotoxin in plasma or serum using limulus amoebocyte lysate components, wherein a mixed aqueous solution comprising:

a) a surfactant selected from a group consisting of polyoxyethylene ethers, polyoxyethylene sorbitans, n-alkylglucopyranosides and dodecyl sulfates;
b) a compound having an imidazolyl or amino group; and
c) an alkaline earth metal salt and an alkaline metal hydroxide; is added to the plasma or serum prior to the assay.

Among the surfactants usable in the present invention, examples of the polyoxyethylene ethers include polyoxyethylene-p-tert-octyl (or iso-octyl) phenyl ether (degree of polymerization: 8–40), polyoxyethylene-4-tert-octyl (or iso-octyl) cyclohexyl ether (degree of polymerization: 8–40), polyoxyethylene-p-nonyl phenyl ether (degree of polymerization: 9–15), polyoxyethylene heptamethyl hexyl ether (degree of polymerization: 10–20) and polyoxyethylene dodecyl ether (degree of polymerization: 10–29). Examples of the n-alkylglucopyranosides include n-(heptyl, octyl, nonyl, decyl or dodecyl)($\alpha$- or $\beta$-)D-glucopyranosides. Examples of the polyoxyethylene sorbitans include polyoxyethylene sorbitan (degree of polymerization: about 20) monolaurate, monopalmitate, monostearate, monooleate and trioleate. Examples of the dodecyl sulfates include sodium dodecyl sulfate, lithium dodecyl sulfate and calcium dodecyl sulfate.

Examples of the compound having an imidazolyl or amino group include histamine dihydrochloride, L-histidine dihydrochloride, poly-L-histidine hydrochloride (molecular weight: 15,000–50,000), poly-L-lysine hydrochloride (molecular weight: 2,000–70,000), poly-L-arginine hydrochloride (molecular weight: 5,000–150,000), polyethyleneimine (molecular weight: 1,000–70,000), adenine hydrochloride and cytosine hydrochloride.

The content of the surfactant a) in the mixed aqueous solution may vary depending on the type but preferably ranges from 0.04 to 0.40% (w/v). The content of the compound b) in the mixed aqueous solution having an imidazolyl or amino group preferably ranges from 0.03 to 0.3% (w/v), though it may vary depending on the type. The contents of the alkaline earth metal salt and the alkaline metal hydroxide in the mixed aqueous solution range from 0.005 to 0.05 mol/l and from 0.05 to 0.5 mol/l respectively.

Further, a clear sample solution without any turbidity can be obtained by adding to the mixed aqueous solution N,N-bis(2-hydroxyethyl)glycine so as to give a concentration of from 0.005 to 0.05 mol/l in the mixed aqueous solution, preferably from 0.02 to 0.05 mol/l.

The plasma or serum may be treated with the mixed aqueous solution at a temperature of from 25° to 70° C., preferably from 37° to 56° C., for 5 to 30 minutes, preferably 5 to 20 minutes.

The sample solution obtained by treating the plasma or serum with the mixed aqueous solution of the present invention comprising the components a) to c) is allowed to react with the limulus amoebocyte lysate components to thereby assay an endotoxin.

BEST MODE FOR PRACTICE OF THE INVENTION

To further illustrate the present invention in greater detail, the following Examples are given, but are not to be construed to limit the scope of the invention.

EXAMPLE 1

Heparin was added to blood collected from a healthy subject so as to give a concentration of 5 units/ml and a 2 ml portion thereof was centrifuged at 150×g for 10 minutes to obtain platelet-rich plasma (PRP).

To 190 $\mu$l of this PRP specimen was added 10 $\mu$l of an aqueous solution of an endotoxin preparation from *Salmonella abortus equi* (Endotoxin Standard NP1) (2 ng/ml) and well mixed. Then, a 5 $\mu$l portion of the resulting mixture was introduced in an endotoxin-free microplate (trade name: Toxipet plate 96 F, commercially available from Seikagaku Corporation). Thereto was added 20 $\mu$l of a mixed aqueous solution prepared by adding polyethyleneimine (ethyleneimine polymer EIP, average molecular weight: 70,000) to an aqueous solution containing 0.1 mol/l of potassium hydroxide (KOH), 0.01 mol/l of calcium chloride ($CaCl_2$) and 0.1% (w/v) of Triton X-100 (trade name of polyoxyethylene-p-tert-octylphenyl ether, commercially available from Rohm & Haas Co.) to give a concentration of 0.016 to 0.800% (w/v). After maintaining at 37° C. for 10 minutes, the resulting solution served as the sample solution.

The endotoxin contained in this sample solution was assayed in the following manner. Endospecy (registered trademark, manufactured by Seikagaku Corporation), which was a preparation produced by removing enzymes reacting with glucan from limulus amoebocyte lysate, was dissolved in 4.4 ml of a 0.1 mol/l Tris hydrochloride buffer (pH 8.0). 100 μl of Endospecy was added to 25 μl of the sample solution and the mixture was incubated at 37° C. for 30 minutes. Then, thereto were successively added 50 μl of 0.04% (w/v) sodium nitrite in 1 mol/l hydrochloric acid, 50 μl of 0.3% (w/v) ammonium sulfamate and 50 μl of 0.07% (w/v) N-1-naphthylethylenediamine dihydrochloride in 14% (v/v) N-methyl-2-pyrrolidone to thereby effect diazo-coupling. The absorbance of the mixture was measured at 550 and 630 nm simultaneously with the latter as a reference with a microplate reader.

Table 1 shows the results of the assay in this Example in which the EIP concentration was varied and the result of a comparative example in which no endotoxin was added.

In Table 1, EIP concentration (%) means the concentration at the treatment. The assay result of the comparative example in which no endotoxin was added is expressed in the absorbance determined at 550-630 nm, while the results of the Example in which the endotoxin was added are expressed in a detection ratio (%) calculated by regarding the data of the control example, in which the PRP specimen was replaced with a physiological saline for injection and the solution for pretreatment was replaced with distilled water for injection, as 100.

TABLE 1

| Sample solution | EIP conc. (%) | Absorbance (no endotoxin) | Detection ratio of added endotoxin (%) |
|---|---|---|---|
|  | 0.000 | 0.027 | 52 |
|  | 0.016 | 0.028 | 55 |
|  | 0.032 | 0.028 | 91 |
| PRP | 0.048 | 0.029 | 100 |
| (+ endotoxin) | 0.064 | 0.029 | 100 |
| + Triton X-100 | 0.080 | 0.029 | 100 |
| + EIP | 0.160 | 0.029 | 100 |
| + KOH | 0.240 | 0.028 | 92 |
| + CaCl$_2$ | 0.320 | 0.028 | 83 |
|  | 0.400 | 0.027 | 70 |
|  | 0.600 | 0.028 | 70 |
|  | 0.800 | 0.026 | 65 |
| Control example | 0.000 | 0.025 | 100 |

As shown in Table 1, a detection ratio of the endotoxin was very low (52%) in the case that the sample solution was treated with only 0.08 mol/l of KOH and 0.008 mol/l CaCl$_2$ and 0.08% Triton X-100, without EIP, and the detection ratio increased with an increase in the EIP concentration.

When EIP concentration exceeded 0.32%, the detection ratio of the endotoxin decreased. It is evident, however, that the limulus test false-positive factors and inhibition factors can be almost completely eliminated when EIP is used in a concentration of approximately 0.032 to 0.240% in the treatment and therefore the true content of the endotoxin in the PRP can be precisely determined at a high reliability and a high reproducibility.

Namely, the fact that the absorbance of the comparative example, in which no endotoxin was used, is the same as that of the control example indicates that the limulus test false-positive factors in the PRP have been completely denatured. Further, the fact that the endotoxin detection ratio of the Example, in which the endotoxin was used, is 100% indicates that the limulus test reaction-inhibiting factors (false-negative factors) in the PRP have been completely denatured. Thus, an ideal condition is that these factors are simultaneously denatured, that is, the data of the comparative example are almost the same as those of the control example and the data of the example are almost 100%, which means that almost all of the endotoxin used in the example can be detected and recovered. As Table 1 shows, the above-mentioned ideal conditions are achieved by using 0.032 to 0.240% of EIP.

EXAMPLE 2

10 μl of an aqueous solution containing 40 pg of an endotoxin preparation E. coli 0111:B4 was added to 190 μl of a PRP specimen prepared in the same manner as in Example 1. Then, 5 μl of the resulting mixture was introduced into a Toxipet plate 96F and 20 μl of a mixed aqueous solution comprising Triton X-100 in a predetermined amount within the range of from 0 to 0.5%, 0.1 mol/l KOH, 0.07% EIP and 0.01 mol/l CaCl$_2$ was added thereto. The mixture was incubated at 37° C. for 10 minutes to obtain a sample solution.

The endotoxin in the thus-obtained sample solution was assayed in the same manner as in Example 1.

Table 2 shows the results of the above-mentioned assay in Example 2, in which the concentration of Triton X-100 was varied, similar to Example 1, together with the result of the comparative example, in which no endotoxin was used, and that of the control example, in which the PRP specimen was replaced with physiological saline and the pretreatment solution was replaced with distilled water for injection.

The result of the comparative example in which no endotoxin was used is expressed in the absorbance determined at 550-630 nm, while the results of the Example in which the endotoxin was used are expressed in a detection ratio (%) calculated by regarding the data of the control example as 100, similar to Example 1.

TABLE 2

| Sample solution | Triton X-100 conc. (%) | Absorbance (no endotoxin) | Detection ratio of added endotoxin (%) |
|---|---|---|---|
|  | 0.00 | 0.025 | 19 |
|  | 0.04 | 0.026 | 85 |
| PRP | 0.06 | 0.028 | 100 |
| (+ endotoxin) | 0.08 | 0.029 | 100 |
| + Triton X-100 | 0.10 | 0.028 | 100 |
| + EIP | 0.12 | 0.029 | 100 |
| + KOH | 0.16 | 0.026 | 64 |
| + CaCl$_2$ | 0.24 | 0.026 | 41 |
|  | 0.32 | 0.026 | 25 |
|  | 0.40 | 0.025 | 8 |
| Control example | 0.00 | 0.025 | 100 |

As shown in Table 2, the specimen treated without using Triton X-100 showed a very low detection ratio of the endotoxin. On the contrary, the PRP specimen treated with a mixed solution containing, for example, 0.06 to 0.12% of Triton X-100 showed an endotoxin detection ratio of 100%.

Therefore, it is evident that the Limulus test false-positive factors and inhibition factors can be almost completely denatured when a mixed aqueous solution containing a predetermined concentration of a surfactant (Triton X-100), 0.08 mol/l KOH, 0.056% EIP and 0.008 mol/l $CaCl_2$ (each showing the concentration at the PRP treatment) and therefore the true content of the endotoxin in the PRP can be precisely determined at a high reliability and a high reproducibility.

EXAMPLE 3

10 μl of an aqueous solution containing 10 pg of an endotoxin preparation *E. coli* UKT-B was added to 190 μl of a PRP specimen prepared in the same manner as in Example 1. Then, 5 μl of the resulting mixture was introduced into a Toxipet plate 96F and 20 μl of a mixed aqueous solution comprising 0.1% Triton X-100, 0.1 mol/l KOH, 0.07% EIP and 0.01 mol/l $CaCl_2$ was added thereto. The mixture was incubated at 37° C. for a definite time to serve as a sample solution.

The endotoxin in the thus-obtained sample solution was assayed in the same manner as in Example 1.

Table 3 shows the results of the above-mentioned assay of Example 3, in which the heating time was varied, together with the result of the comparative example, in which no endotoxin was added, and that of the control example, in which the PRP specimen was replaced with physiological saline and the pretreatment solution was replaced with distilled water for injection, similar to Example 1.

TABLE 3

| Sample solution | Heating time (min) | Absorbance (no endotoxin) | Detection ratio of added endotoxin (%) |
|---|---|---|---|
| PRP | 0 | 0.025 | 12 |
| (+ endotoxin) | 5 | 0.026 | 94 |
| + Triton X-100 | 10 | 0.028 | 100 |
| + EIP | 15 | 0.029 | 100 |
| + KOH | 20 | 0.028 | 100 |
| + $CaCl_2$ | 30 | 0.029 | 71 |
| Control example | | 0.025 | 100 |

As shown in Table 3, the unheated specimen which was obtained immediately after the treatment with the pretreatment mixed solution showed a very low detection ratio of the endotoxin. On the contrary, it is evident that the limulus test false-positive factors and inhibition factors can be almost completely denatured when a sample solution was heated for 5 minutes or longer and therefore the true content of the endotoxin in the PRP can be precisely determined at a high reliability and a high reproducibility.

EXAMPLE 4

10 μl of an aqueous solution containing 40 pg of an endotoxin preparation *E. coli* 0111:B4 was added to 190 μl of a PRP specimen prepared in the same manner as in Example 1. Then, 5 μl of the resulting mixture was introduced into a Toxipet plate 96F and 20 μl of a mixed aqueous solution comprising 0.1% Triton X-100, 0.1 mol/l KOH, 0.07% EIP and 0.01 mol/l $CaCl_2$ was added thereto. The mixture was incubated at a definite temperature for 10 minutes to serve as a sample solution.

The endotoxin in the thus-obtained sample solution was assayed in the same manner as in Example 1.

Table 4 shows the results of the above-mentioned assay of Example 4, in which the heating temperature was varied, together with the result of the comparative example, in which no endotoxin was added, and that of the control example, in which the PRP specimen was replaced physiological saline and the pretreatment solution was replaced with distilled water for injection, similar to Example 1.

TABLE 4

| Sample solution | Heating temp (°C.) | Absorbance (no endotoxin) | Detection ratio of added endotoxin (%) |
|---|---|---|---|
| PRP | 4 | 0.026 | 22 |
| (+ endotoxin) | 20 | 0.029 | 85 |
| + Triton X-100 | 25 | 0.029 | 91 |
| + EIP | 37 | 0.030 | 100 |
| + KOH | 45 | 0.031 | 100 |
| + $CaCl_2$ | 56 | 0.031 | 100 |
| | 70 | 0.027 | 82 |
| Control example | | 0.025 | 100 |

As shown in Table 4, the specimen treated at 4° C. showed a very low detection ratio of the endotoxin. On the contrary, it is evident that the limulus test false-positive factors and inhibition factors can be almost completely denatured when a sample solution is treated at 25° C. or above and therefore the true content of the endotoxin in the PRP can be precisely determined at a high reliability and a high reproducibility.

EXAMPLE 5

Heparin was added to blood collected from a healthy subject so as to give a concentration of 5 U/ml and a 2 ml portion thereof was centrifuged at 1,000 ×g for 10 minutes to obtain a platelet-poor plasma (PPP).

To 190 μl of a PPP specimen thus prepared was added 10 μl of an aqueous solution containing 40 pg of an endotoxin preparation *E. coli* 0111:B4. Then, 5 μl of the resulting mixture was introduced into a Toxipet plate 96F and 20 μl of a mixed aqueous solution comprising Tween 20 (trade name, available from Wako Pure Chemical Industries) which is polyoxyethylene sorbitan monolaurate in a definite amount selected within the range of from 0 to 1.0% (w/v), 0.1 mol/l KOH, 0.1% (w/v) histamine dihydrochloride and 0.01 mol/l $CaCl_2$ was added thereto. The mixture was incubated at 37° C. for 10 minutes to serve as a sample solution.

The endotoxin in the sample solution was assayed in the same manner as in Example 1.

Table 5 shows the results of the above-mentioned assay of Example 5, in which the concentration of Tween 20 was varied, together with the result of the comparative example, in which no endotoxin was added, and that of the control example, in which the PPP specimen was replaced with physiological saline and the pretreatment solution was replaced with distilled water for injection, similar to Example 1.

TABLE 5

| Sample solution | Tween 20 conc. (%) | Absorbance (no endotoxin) | Detection ratio of added endotoxin (%) |
|---|---|---|---|
| PPP | 0.00 | 0.025 | 19 |
| (+ endotoxin) | 0.08 | 0.026 | 57 |
| + Tween 20 | 0.16 | 0.028 | 84 |
| + histamine dihydrochloride | 0.24 | 0.029 | 95 |
| + KOH | 0.32 | 0.028 | 100 |
| + $CaCl_2$ | 0.40 | 0.029 | 100 |
| | 0.60 | 0.026 | 55 |
| | 0.80 | 0.026 | 0 |
| Control example | 0.00 | 0.025 | 100 |

As Table 5 clearly shows, the limulus test false-positive factors and inhibition factors can be almost completely denatured when a surfactant (Tween 20) is used in a predetermined appropriate concentration and therefore the true content of the endotoxin in the PPP specimen can be precisely determined at a high reliability and a high reproducibility. On the other hand, the specimen treated with the mixed solution containing 0.08 mol/l KOH, 0.08% histamine dihydrochloride and 0.008 mol/l CaCl$_2$ but containing no Tween 20 showed a very low detection ratio of the endotoxin.

EXAMPLE 6

10 μl of an aqueous solution containing 40 pg of an endotoxin preparation E. coli 0111:B4 was added to 190 μl of a PPP specimen prepared in the same manner as in Example 5. Then, 5 μl of the resulting mixture was introduced into a Toxipet plate 96F and 20 μl of a mixed aqueous solution comprising sodium dodecyl sulfate (SDS) in a definite amount selected within the range of from 0 to 1.0% (w/v), 0.1 mol/l KOH, 0.05% (w/v) ε-poly-L-lysine hydrochloride (molecular weight: 2,000–4,000; commercially available from Wako Pure Chemicals Industries) and 0.01 mol/l CaCl$_2$ was added thereto. The mixture was incubated at 37° C. for 10 minutes to serve as a sample solution.

The endotoxin in the sample solution was assayed in the same manner as in Example 1.

Table 6 shows the results of the above-mentioned assay of Example 6, in which the concentration of SDS was varied, together with the result of the comparative example, in which no endotoxin was added, and that of the control example, in which the PPP specimen was replaced with physiological saline and the pretreatment solution was replaced with distilled water for injection, similar to Example 1.

TABLE 6

| Sample solution | SDS conc. (%) | Absorbance (no endotoxin) | Detection ratio of added endotoxin (%) |
| --- | --- | --- | --- |
|  | 0.00 | 0.025 | 20 |
| PPP | 0.08 | 0.025 | 45 |
| (+ endotoxin) | 0.16 | 0.027 | 87 |
| + SDS | 0.24 | 0.030 | 100 |
| + poly-L-lysine hydrochloride | 0.32 | 0.030 | 100 |
| + KOH | 0.40 | 0.030 | 90 |
| + CaCl$_2$ | 0.60 | 0.027 | 22 |
|  | 0.80 | 0.026 | 0 |
| Control example | 0.00 | 0.025 | 100 |

As Table 6 shows, the limulus test false-positive factors and inhibition factors can be almost completely denatured when a surfactant (SDS) is used in a predetermined appropriate concentration, and therefore the true content of the endotoxin in the PPP specimen can be precisely determined at a high reliability and a high reproducibility.

EXAMPLE 7

3 ml of blood, which had been collected from a healthy subject without using any anticoagulant, was allowed to stand at 4° C. for 1 hour and then centrifuged at 1,000 ×g for 10 minutes to obtain serum.

10 μl of an aqueous solution containing 40 pg of an endotoxin preparation E. coli 0111:B4 was added to 190 μl of this serum specimen. Then, 5 μl of the resulting mixture was introduced into a Toxipet plate 96F and 20 μl of a mixed aqueous solution comprising n-octyl-β-D-glucopyranoside in a definite amount selected within the range of from 0 to 1.0% (w/v), 0.1 mol/l KOH, 0.07% EIP and 0.01 mol/l CaCl$_2$ was added thereto. The mixture was incubated at 37° C. for 10 minutes to serve as a sample solution.

The endotoxin in the sample solution was assayed in the same manner as in Example 1.

Table 7 shows the results of the above-mentioned assay of Example 7, in which the concentration of n-octylglucoside was varied, together with the result of the comparative example, in which no endotoxin was added, and that of the control example, in which the serum specimen was replaced with physiological saline and the pretreatment solution was replaced with distilled water for injection, similar to Example 1.

TABLE 7

| Sample solution | n-Octyl-glucoside conc. (%) | Absorbance (no endotoxin) | Detection ratio of added endotoxin (%) |
| --- | --- | --- | --- |
|  | 0.00 | 0.026 | 20 |
| Serum | 0.08 | 0.026 | 65 |
| (+ endotoxin) | 0.16 | 0.029 | 82 |
| + n-octyl-glucoside | 0.24 | 0.029 | 100 |
| + EIP | 0.32 | 0.029 | 100 |
| + KOH | 0.40 | 0.029 | 84 |
| + CaCl$_2$ | 0.60 | 0.026 | 36 |
|  | 0.80 | 0.026 | 2 |
| Control example | 0.00 | 0.025 | 100 |

As Table 7 shows, the limulus test false-positive factors and inhibition factors can be almost completely denatured when a surfactant (n-octylglucoside) is used in a predetermined appropriate concentration and therefore the true content of the endotoxin in the serum specimen can be precisely determined at a high reliability and a high reproducibility.

EXAMPLE 8

The anticoagulant (heparin) was added to bloods collected from various test animals including mice (ICR, male), rats (Wistar, male), guinea pigs (Hartley, male), rabbits (JW, male) and dogs (Beagle, male) and PRP specimens were obtained therefrom in the same manner as in

EXAMPLE 1.

To 190 μl of each PRP specimen thus prepared was added 10 μl of an aqueous solution containing 40 pg of an endotoxin preparation E. coli 0111: B4. Then, 5 μl of the resulting mixture was introduced into a Toxipet plate 96F and 20 μl of a mixed aqueous solution comprising 0.1% Triton X-100, 0.1 mol/l KOH, 0.07% EIP and 0.01 mol/l CaCl$_2$ was added thereto. The mixture was incubated at 37° C for 10 minutes to serve as a sample solution.

The endotoxin in the thus-obtained sample solution was assayed in the same manner as in Example 1.

Table 8 shows the results of the above-mentioned assay together with the result of the comparative example, in which no endotoxin was added, and that of the control example, in which the PRP specimen was replaced with physiological saline and the pretreatment solution was replaced with distilled water for injection, similar to Example 1.

TABLE 8

| Sample solution | Animal (PRP) | Absorbance (no endotoxin) | Detection ratio of added endotoxin (%) |
|---|---|---|---|
| PRP | mouse | 0.029 | 100 |
| (+ endotoxin) | rat | 0.028 | 99 |
| + Triton X-100 | guinea pig | 0.029 | 100 |
| + EIP | rabbit | 0.031 | 99 |
| + KOH | dog | 0.031 | 99 |
| + CaCl$_2$ | | | |
| Control example | | 0.025 | 100 |

According to Table 8, a detection ratio was almost 100% in each sample solution.

Thus, good results were obtained in the case of using a limited amount of samples obtained from small test animals, which indicates that the method of the present invention has achieved remarkable improvements not only in quickness and convenience but also in the specificity of the treatment of specimens.

EXAMPLE 9

Triton X-100, KOH, EIP and CaCl$_2$ were mixed together so as to give concentrations in an aqueous solution of 0.1%, 0.1 mol/l, 0.07% and 0.01 mol/l, respectively. Thereto was further added a definite amount selected within a range of from 0 to 0.06 mol/l of N,N-bis(2-hydroxyethyl)glycine (Bicine, trade name of Dotite reagent commercially available from Wako Pure Chemical Industries). The resulting mixture was maintained under ice-cooling for a definite time. Table 9 shows the results of the observation in Example 9, in which the concentration of Bicine was varied, together with that of the comparative example in which no Bicine was added.

TABLE 9

| Sample solution | Bicine conc. (mol/l) | Turbidity after 2 hr |
|---|---|---|
| + Triton X-100 | 0.000 | ++ |
| + EIP | 0.005 | + |
| + KOH | 0.010 | + |
| + CaCl$_2$ | 0.020 | − |
| + Bicine | 0.048 | − |

−: no change.
+: slight milky turbidity.
++: milky turbidity.

According to Table 9, an aqueous solution containing Triton X-100, KOH, EIP and CaCl$_2$ each in a definite amount, without Bicine, became turbid after preservation under ice-cooling for 2 hours. In this case, it was therefore impossible to uniformly collect samples. On the contrary, the addition of Bicine prevented the solution from becoming turbid. In particular, an aqueous solution containing Bicine in a concentration of 0.02 mol/l or more remained transparent after 2 hours and thus it can be uniformly collected.

Example 10

To 190 μl of a PRP specimen prepared in the same manner as in Example 1 was added 10 μl of an aqueous solution containing 40 pg of an endotoxin preparation E. coli 0111:B4. Then, 5 μl of the resulting mixture was introduced into a Toxipet plate 96F and 20 μl of a mixed aqueous solution comprising 0.1% Triton X-100, 0.1 mol/l KOH, 0.03 mol/l Bicine, 0.07% EIP and 0.01 mol/l CaCl$_2$, which had been mixed and allowed to stand under ice-cooling for 2 hours, was added thereto. The mixture was incubated at 37° C. for 10 minutes to serve as a sample solution.

The endotoxin in the thus-obtained sample solution was assayed in the same manner as in Example 1.

Table 10 shows the results of the above-mentioned assay together with the result of the comparative example, in which no endotoxin was added, and that of the control example, in which the PRP specimen was replaced with physiological saline and the pretreatment solution was replaced with distilled water for injection, similar to Example 1.

TABLE 10

| Sample solution | Preservation time (hr) | Absorbance (no endotoxin) | Detection ratio of added endotoxin (%) |
|---|---|---|---|
| PRP | 0 | 0.029 | 100 |
| (+ endotoxin) | 2 | 0.029 | 100 |
| + Triton X-100 | | | |
| + EIP | | | |
| + KOH | | | |
| + CaCl$_2$ | | | |
| + Bicine | | | |
| Control example | | 0.025 | 100 |

According to Table 10, almost 100% of the endotoxin detection ratio could be achieved in the case of using the mixed aqueous solution comprising the definite amounts of Triton X-100, KOH, EIP, CaCl$_2$ and Bicine either immediately after the preparation or after preservation under ice-cooling for 2 hours. This means that the addition of an appropriate amount of Bicine would inhibit the cloudiness of the treatment solution and elevate its stability.

EXAMPLE 11

To 190 μl of a PRP specimen prepared in the same manner as in Example 1 was added 10 μl of an aqueous solution containing 40 pg of an endotoxin preparation E. coli 0111:B4. Then, 5 μl of the resulting mixture was introduced into a Toxipet plate 96F and 20 μl of a mixed aqueous solution comprising 0.1% Triton X-100, 0.1 mol/l sodium hydroxide (NaOH), 0.03 mol/l Bicine, 0.07% EIP and 0.01 mol/l CaCl$_2$ was added thereto as well as 20 μl of the same mixed aqueous solution, which had been allowed to stand under ice-cooling for 2 hours. The mixture was incubated at 37° C. for 10 minutes to serve as a sample solution.

The endotoxin in the thus-obtained sample solution was assayed in the same manner as in Example 1.

Table 11 shows the results of the above-mentioned assay together with the result of the comparative example, in which no endotoxin was added, and that of the control example, in which the PRP specimen was replaced with physiological saline and the pretreatment solution was replaced with distilled water for injection, similar to Example 1.

TABLE 11

| Sample solution | Preservation time (hr) | Absorbance (no endotoxin) | Detection ratio of added endotoxin (%) |
|---|---|---|---|
| PRP | 0 | 0.028 | 92 |
| (+ endotoxin) | 2 | 0.028 | 91 |
| + Triton X-100 | | | |
| + EIP | | | |
| + NAOH | | | |
| + CaCl$_2$ | | | |
| + Bicine | | | |
| Control example | | 0.025 | 100 |

EXAMPLE 12

To 190 μl of a PRP specimen prepared in the same manner as in Example 1 was added 10 μl of an aqueous solution containing 40 pg of an endotoxin preparation E. coli 0111:B4. Then, 5 μl of the resulting mixture was introduced into a Toxipet plate 96F and 20 μl of a mixed aqueous solution comprising 0.1% Triton X-100, 0.1 mol/l KOH, 0.03 mol/l Bicine, 0.07% EIP and 0.02 mol/l magnesium chloride ($MgCl_2$) was added thereto as well as 20 μl of the same mixed aqueous solution, which had been mixed and allowed to stand under ice-cooling for 2 hours. The mixture was incubated at 37° C. for 10 minutes to serve as a sample solution.

The endotoxin in the thus-obtained sample solution was assayed in the same manner as in Example 1.

Table 12 shows the results of the above-mentioned assay together with the result of the comparative example, in which no endotoxin was added, and that of the control example, in which the PRP specimen was replaced with physiological saline and the pretreatment solution was replaced with distilled water for injection, similar to Example 1.

TABLE 12

| Sample solution | Preservation time (hr) | Absorbance (no endotoxin) | Detection ratio of added endotoxin (%) |
|---|---|---|---|
| PRP (+ endotoxin) + Triton X-100 + EIP + KOH + $MgCl_2$ + Bicine | 0 | 0.027 | 90 |
|  | 2 | 0.027 | 91 |
| Control example |  | 0.025 | 100 |

EXAMPLE 13

Assay of plasma specimen

Blood was aseptically collected from, with adding heparin, 30 healthy subjects and 10 patients suffering from serious blood diseases (for example, leukemia) with being doubted to be septicemia due to gram-negative bacteria and hepatic/biliary diseases complicated with infectious diseases. The blood sample was centrifuged at 4° C. at 150 ×g for 10 minutes to thereby give a PRP specimen. Then, 5 μl of the resulting specimen was introduced into a Toxipet plate 96F and 20 μl of a mixed aqueous solution comprising 0.1% Triton X-100, 0.1 mol/l KOH, 0.03 mol/l Bicine, 0.07% EIP and 0.01 mol/l $CaCl_2$ was added thereto. The mixture was incubated at 37° C. for 10 minutes to serve as a sample solution.

The endotoxin in the thus-obtained sample solution was assayed in the same manner as in Example 1.

Table 13 shows the results of this Example expressed in the contents of E. coli 0111: B4 endotoxin calculated by using a calibration curve which had been separately prepared.

TABLE 13

| Specimen | Endotoxin (pg/ml) |
|---|---|
| Healthy subjects (30) | 2.1 ± 1.6 |
| Patient |  |
| 1 | 23.5 |
| 2 | 49.9 |
| 3 | 64.2 |
| 4 | 18.6 |
| 5 | 27.4 |

TABLE 13-continued

| Specimen | Endotoxin (pg/ml) |
|---|---|
| 6 | 17.0 |
| 7 | 24.5 |
| 8 | 30.5 |
| 9 | 31.7 |
| 10 | 55.1 |

The patients 1 to 10 listed in Table 13 were diagnosed as suspected cases of gram-negative bacterial septicemia based on the results of examinations including blood culture and leukocyte counts as well as clinical symptoms such as fever. According to the method of the present invention, endotoxin was detected in each case at a high concentration (30 healthy subjects: 2.1±1.6 pg/ml). It can be understood, therefore, that the assay method of the present invention is to be evaluated as highly useful for quickly diagnosing gram-negative bacterial septicemia which can be hardly diagnosed by conventional test methods.

When plasma or serum is treated with the mixed aqueous solution of the present invention, an endotoxin adsorbed by proteins, lipids, glycoproteins, glycolipids and platelets can be efficiently liberated and thus the endotoxin contained in the plasma or serum can be efficiently assayed at a high detection ratio.

What is claimed is:

1. A method of assaying an endotoxin in a sample by using limulus amoebocyte lysate components, which comprises the steps of, adding to a sample selected from the group consisting of plasma and serum, an aqueous reagent solution comprising:

a) a surfactant selected from the group consisting of polyoxyethylene ethers, polyoxyethylene sorbitans, n-alkylglucopyranosides and dodecyl sulfates;
   b) a compound having an imidazolyl or an amino group; and
   c) an alkaline earth metal salt and an alkaline metal hydroxide;

incubating the resulting mixture under conditions such that the endotoxin is liberated into the reagent solution, and assaying for the endotoxin in the reagent solution using limulus amoebocyte lysate, wherein said polyoxyethylene ethers are selected from the group consisting of polyoxyethylene-p-tert-octyl (or iso-octyl) phenyl ether (degree of polymerization: 8–40), polyoxyethylene-4-tert-octyl (or iso-octyl) cyclohexyl ether (degree of polymerization: 8–40), polyoxyethylene-p-nonyl phenyl ether (degree of polymerization: 9–15), polyoxyethylene heptamethyl hexyl ether (degree of polymerization: 10–20) and polyoxyethylene dodecyl ether (degree of polymerization: 10–29); said n-alkylglucopyranosides are selected from the group consisting of n-(heptyl, octyl, nonyl, decyl and dodecyl)α-D-glucopyranosides and n-(heptyl, octyl, nonyl, decyl and dodecyl)β-D-glucopyranosides; said polyoxyethylene sorbitans are selected from the group consisting of monolaurate, monopalmitate, monostearate, monooleate and trioleate of polyoxyethylene sorbitan (degree of polymerization: about 20); said dodecyl sulfates are selected from the group consisting of sodium dodecyl sulfate, lithium dodecyl sulfate and calcium dodecyl sulfate; and said compound having an imidazolyl group or an amino group is selected from the group consisting of histamine dihydrochloride, L-histidine dihydrochloride, poly-L-histidine hydrochloride, poly-L-lysine hydrochloride, poly-L-arginine hydrochloride, polyethyleneimine, adenine hydrochloride and cytosine hydrochloride;

wherein said alkaline earth metal salt is a water soluble salt of an alkaline earth metal with an inorganic or an organic acid;

wherein said alkaline earth metal is a metal selected from the group consisting of calcium, magnesium and strontium; and wherein said inorganic acid or organic acid is an acid selected from the group consisting of hydrochloric acid, nitric acid, sulfuric acid, acetic acid and citric acid.

2. A method as claimed in claim 1, wherein said aqueous reagent solution contains N,N-bis(2-hydroxyethyl)glycine.

3. A method as claimed in claim 2, wherein said N,N-bis(2-hydroxyethyl)glycine is present in said aqueous reagent solution in a concentration of from 0.005 to 0.05 mol/l.

4. A method as claimed in claim 1, wherein said aqueous reagent solution contains said surfactant in a concentration of from 0.04 to 0.40% (w/v), said compound having an imidazolyl group or an amino group in a concentration of from 0.03 to 0.3% (w/v), said alkaline earth metal salt in a concentration of from 0,005 to 0.05 mol/l and said alkaline metal hydroxide in a concentration of from 0.05 to 0.5 mol/l.

5. A method as claimed in claim 1, wherein the incubating is carried out at 25° to 70° C. for 5 to 30 minutes.

6. A method of pretreating a sample to be assayed for an endotoxin using limulus amoebocyte lysate components, which comprises the steps of:

adding to a sample selected from the group consisting of plasma and serum an aqueous reagent solution comprising:

a) a surfactant selected from the group consisting of polyoxyethylene ethers, polyoxyethylene sorbitans, n-alkylglucopyranosides and dodecyl sulfates;

b) a compound having an imidazolyl or an amino group; and c) an alkaline earth metal salt and an alkaline metal hydroxide; and incubating the resulting mixture under conditions such that the endotoxin is liberated into the reagent solution, wherein said polyoxyethylene ethers are selected from the group consisting of polyoxyethylene-p-tert-octyl (or iso-octyl) phenyl ether (degree of polymerization: 8–40), polyoxyethylene-4-tert-octyl (or iso-octyl) cyclohexyl ether (degree of polymerization: 8–40), polyoxyethylene-p-nonyl phenyl ether (degree of polymerization: 9–15), polyoxyethylene heptamethyl hexyl ether (degree of polymerization: 10–20) and polyoxyethylene dodecyl ether (degree of polymerization: 10–29); said n-alkylglucopyranosides are selected from the group consisting of n-(heptyl, octyl, nonyl, decyl and dodecyl) α-D-glucopyranosides and n-(heptyl, octyl, nonyl, decyl and dodecyl) β-D-glucopyranosides; said polyoxyethylene sorbitans are selected from the group consisting of monolaurate, monopalmitate, monostearate, monooleate and trioleate of polyoxyethylene sorbitan (degree of polymerization: about 20); said dodecyl sulfates are selected from the group consisting of sodium dodecyl sulfate, lithium dodecyl sulfate and calcium dodecyl sulfate; and said compound having an imidazolyl group or an an amino group is selected from the group consisting of histamine dihydrochloride, L-histidine dihydrochloride, poly-L-histidine hydrochloride, poly-L-lysine hydrochloride, poly-L-arginine hydrochloride, polyethyleneimine, adenine hydrochloride and cytosine hydrochloride;

wherein said alkaline earth metal salt is a water soluble salt of an alkaline earth metal with an inorganic or an organic acid;

wherein said alkaline earth metal is a metal selected from the group consisting of calcium, magnesium and strontium; and wherein said inorganic acid or organic acid is an acid selected from the group consisting of hydrochloric acid, nitric acid, sulfuric acid, acetic acid and citric acid.

* * * * *